United States Patent
Lee et al.

(10) Patent No.: US 7,253,212 B2
(45) Date of Patent: Aug. 7, 2007

(54) RETINOL DERIVATIVE AND COSMETIC COMPOSITION COMPRISING THE SAME

(75) Inventors: Kun-Su Lee, Seoul (KR); Jee-Hean Jeong, Suwon-shi (KR); Seung-Ji Lee, Cheonan-shi (KR); Jung-No Lee, Chungcheongnam-do (KR); Byong-Kee Jo, Anyang-shi (KR)

(73) Assignee: Coreana Cosmetics Co., Ltd., Cheonan-shi (KR)

( * ) Notice: Subject to any disclaimer, the term of this patent is extended or adjusted under 35 U.S.C. 154(b) by 518 days.

(21) Appl. No.: 10/504,861

(22) PCT Filed: Dec. 18, 2002

(86) PCT No.: PCT/KR02/02383

§ 371 (c)(1),
(2), (4) Date: Nov. 4, 2004

(87) PCT Pub. No.: WO2004/054992

PCT Pub. Date: Jul. 1, 2004

(65) Prior Publication Data

US 2005/0148660 A1 Jul. 7, 2005

(51) Int. Cl.
*A01N 31/04* (2006.01)
*A01N 43/08* (2006.01)
*C07C 49/00* (2006.01)
(52) U.S. Cl. ........................ 514/725; 514/474; 568/378
(58) Field of Classification Search .................... None
See application file for complete search history.

(56) References Cited

U.S. PATENT DOCUMENTS 5,516,793 A  5/1996  Duffy

FOREIGN PATENT DOCUMENTS

WO    99/53904    10/1999

*Primary Examiner*—Jon Weber
*Assistant Examiner*—Paul Martin
(74) *Attorney, Agent, or Firm*—Nixon & Vanderhye P.C.

(57) ABSTRACT

The present invention relates to a novel retinol derivative and a cosmetic composition comprising the same, in particular, to a novel retinol derivative represented by the formula (I) exhibiting the effects from both L-ascorbic acid and retinol as well as being free from the disadvantages of two compounds such as skin irritation and instability in cosmetic formulation, and a cosmetic composition comprising the retinol derivative. (I)

6 Claims, 1 Drawing Sheet

RETINOL DERIVATIVE AND COSMETIC COMPOSITION COMPRISING THE SAME

This application is the US national phase of international application PCT/KR02/02383 filed 18 Dec. 2002, which designated the US. The entire contents of this application is incorporated herein by reference.

BACKGROUND OF THE INVENTION

1. Field of the Invention

The present invention relates to a novel retinol derivative and a cosmetic composition comprising the same, in particular, to a novel retinol derivative exhibiting the effects from both L-ascorbic acid and retinol as well as being free from the disadvantages of two compounds such as skin irritation and instability in cosmetic formulation, and a cosmetic composition comprising the retinol derivative.

2. Description of the Related Art

Various reasons may lead to skin spots such as freckles. The main reason is ultraviolet radiation. When skin is exposed to ultraviolet ray, melanin is generated in melanocytes and released and deposited on epidermis, resulting in formation of skin spots such as freckles. In the process of melanin generation in melanocytes, tyrosinase catalyzes the formation of DOPAquinone using tyrosine as substrate and then DOPAquinone undergoes spontaneous reaction and enzyme reaction to generate a copolymeric black pigment, melanin. Thus, to maintain a clear and fair skin, it is necessary to inhibit melanin biosynthesis in melanocytes and the deposition of melanin on skin.

L-ascorbic acid (Vitamin C) exerts good antioxidizing property, inhibition of melanin biosynthesis in melanocytes and enhancement of collagen biosynthesis in fibroblast, so that it is generally used as active ingredient in cosmetics for whitening skin color or eliminating wrinkle. However, L-ascorbic acid has a limitation as cosmetic material due to instability in cosmetic formulation. In order to overcome such disadvantage, several derivatives, which include AA-2P (L-ascorbic acid 2-phosphate), AA-2S (L-ascorbic acid 2-sulfate), AA-6G (6-O-α-D-glucopyranosyl-L-ascorbic acid) and AA-2G (2-O-α-D-glucopyranosyl-L-ascorbic acid), have been developed and employed in place of L-ascorbic acid as cosmetic ingredient.

Skin aging is ascribed to intrinsic aging and photo aging and the latter is believed to a main factor for skin aging. Photo aging is likely to be a cumulative result of the changes occurring in skin such as wrinkles, thickening, flaccidity, decreased elasticity, roughness, dryness and spots, which are attributed to aging by sunlight, in particular, ultraviolet. In other words, skin aging by sunlight may cause the changes in epidermis and dermis, thereby giving rise to wrinkles, thickening and decreased elasticity of skin.

Retinol (Vitamin A) has been well known as cosmetic material for treating and preventing skin aging (U.S. Pat. Nos. 4,603,146 and 4,877,805). Retinoid useful for skin caring includes retinol (vitamin A alcohol), retinal (vitamin A aldehyde) and retinyl acetate, retinyl propionate, retinyl linoleate and retinyl palmitate as retinyl esters. Among them, retinol found in human cell is pivotal in differentiation and growth of epithelial tissue and exhibits higher stability than other retinoids, which enable popular employment of retinol as cosmetic material. However, retinol having the superior effects in treatment and prevention of wrinkle and acne has some disadvantages: (a) as formulated, the changes of color and odor and the reduced efficacy; and (b) skin irritation while low level of retinol is used. Therefore, the use of retinol as cosmetic material has been highly limited.

SUMMARY OF THE INVENTION

Endeavoring to develop novel compound exhibiting synergic effect of L-ascorbic acid and retinol as well as being free from the disadvantages of the two compounds, the present inventors have developed novel retinol derivative exhibiting better whitening effect and treating and preventing effect of wrinkle than L-ascorbic acid and retinol as well as highly decreased irritation and better stability in cosmetic formulation.

Accordingly, it is an object of this invention to provide a novel retinol derivative.

It is another object of this invention to provide a cosmetic composition comprising the retinol derivative as active ingredient.

Other objects and advantages of the present invention will become apparent from the detailed description to follow taken in conjugation with the appended claims and drawings.

DETAILED DESCRIPTION OF THIS INVENTION

Figure 1:
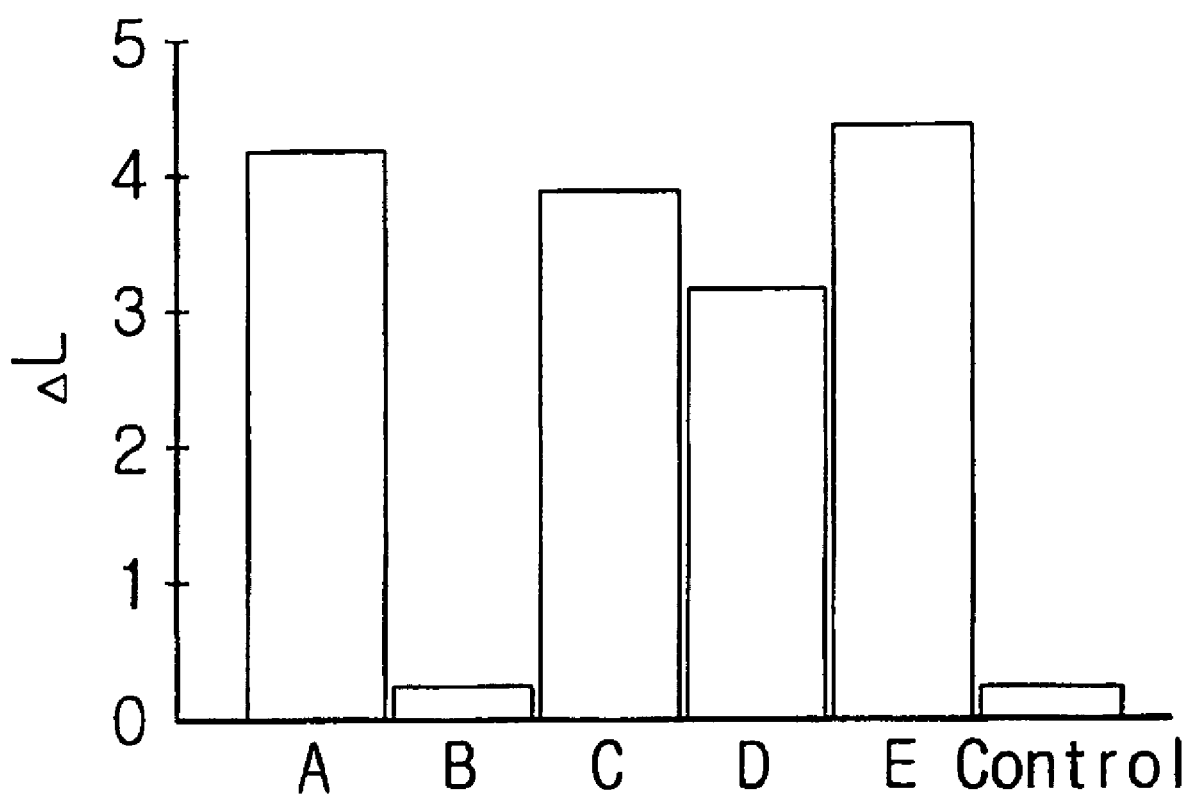
FIG. 1 is a graph showing improved whitening effect of the present retinol derivative. Alphabets on x-axis denote the formulations of Table I.

In one aspect of this invention, there is provided a retinol derivative represented by the following formula (I):

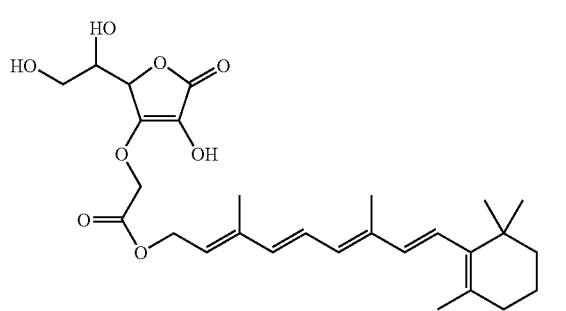

L-ascorbic acid (Vitamin C) is known to have antioxidizing activity, inhibition of melanin biosynthesis in melanocytes (whitening effect) and enhancement of collagen biosynthesis (treating and preventing wrinkle). However, L-ascorbic acid has a limitation as cosmetic material due mainly to instability in cosmetic formulation. Retinol capable of promoting the differentiation and growth of epithelial tissue is known to have the superior effect in treatment and prevention of wrinkle. However, in cosmetic formulation, the color and odor of retinol are very likely to be changed and the efficacy of retinol is likely to be reduced. In addition, as applied to skin, retinol is apt to induce irritation. Therefore, the use of retinol is considerably restricted in cosmetic composition.

The present inventors have made intensive studies to develop a novel compound exhibiting better efficacy than L-ascorbic acid and retinol as well as being free from the shortcomings previously described.

In the novel retinol derivative of this invention, L-ascorbic acid is linked to carbon-15 of retinol through a diester bond rather than direct linkage. Hydroxyl group of carbon-3 of L-ascorbic acid is involved in the linkage to retinol, which is one of structural features of this retinol derivative. While L-ascorbic acid has several reactive hydroxyl groups, only hydroxyl group of carbon-3 is involved in the linkage to retinol in the present retinol derivative. This is because that the hydroxyl group of carbon-3 of L-ascorbic acid is the most reactive group and the hydroxyl group of carbon-2 plays a very important role in exhibiting an activity of L-ascorbic acid.

The present derivative is prepared through (a) esterification of retinol and (b) reaction between esterified retinol and L-ascorbic acid. One example of preparing method for the present derivative is as follows:

(1) Esterification of Retinol with Bromo Acetic Acid

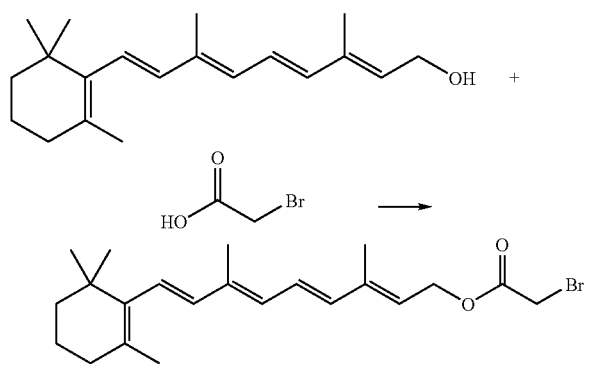

(2) Reaction between Esterified Retinol and L-Ascorbic Acid

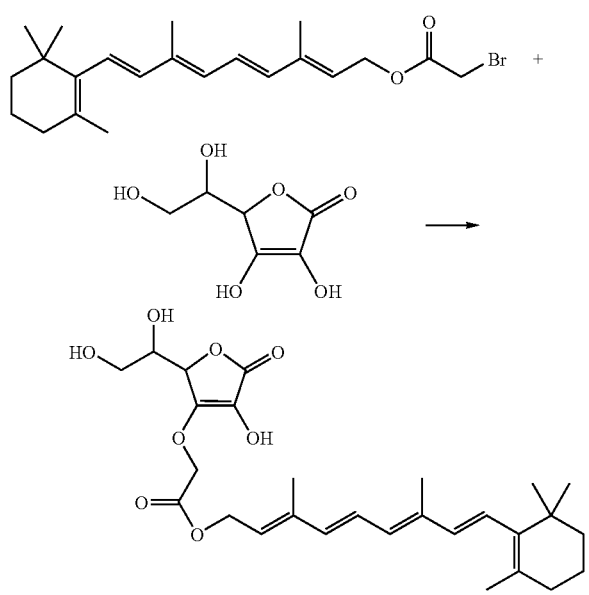

The novel retinol derivative of this invention is found to exhibit better efficacies (e.g. enhancement of collagen biosynthesis, inhibition of melanin generation and antioxidation) than L-ascorbic acid and retinol as well as to overcome the shortcomings of the compounds (e.g. instability in formulation and induction of skin irritation).

Therefore, the novel retinol derivative of this invention can be used as active ingredient in cosmetic composition for skin whitening and/or skin caring (e.g. treating and preventing wrinkles).

In another aspect of this invention, there is provided a cosmetic composition comprising: (a) a cosmetically effective amount of a retinol derivative represented by the following formula (I); and (b) a cosmetically acceptable carrier:

(I)

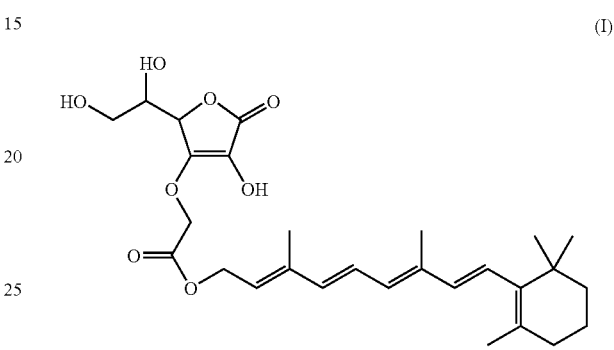

Since the present composition employs the retinol derivative represented by the formula (I) as active ingredient, the common descriptions between them are omitted in order to avoid the complexity of this specification leading to undue multiplicity.

The cosmetic composition of this invention represents a variety of efficacies including enhancement of collagen biosynthesis, antioxidation, inhibition of tyrosinase activity, inhibition of melanin generation, skin whitening, and treatment and prevention of wrinkle, which are ascribed to the retinol derivative represented by the formula (I). These efficacies are found to be better than those of L-ascorbic acid and retinol.

Preferably, the amount of the retinol derivative ranges from 0.0001 to 10.0 wt % based on the total weight of the composition. If the amount of the retinol derivative is lower than 0.0001, the efficacies originated from the derivative may be negligible; in the case of exceeding 10.0 wt %, the efficacies of retinol derivative in parallel with the increase of amount may be rarely represented and the side effects such as induction of skin irritation and instability in formulation may be become apparent. Therefore, it is more advantageous that the amount of the retinol derivative is in the range of 0.0005 to 10.0 wt %, more preferably, 0.05 to 10.0 wt % and most preferably, 1.0 to 3.0 wt % based on the total weight of the composition. The present composition comprising the most preferable amount of the retinol derivative is found to exert much better efficacies than L-ascorbic acid and retinol and to be completely free from the shortcomings of the conventional compounds.

The cosmetic compositions of this invention may be formulated in a wide variety of forms, for example, including a solution, a suspension, an emulsion, a paste, an ointment, a gel, a cream, a lotion, a powder, a soap, a surfactant-containing cleanser, an oil, a powder foundation, an emulsion foundation, a wax foundation and a spray.

The cosmetically acceptable carrier contained in the present cosmetic composition, may be varied depending on the type of the formulation. For example, the formulation of ointment, pastes, creams or gels may comprise animal and vegetable fats, waxes, paraffins, starch, tragacanth, cellulose derivatives, polyethylene glycols, silicones, bentonites, silica, talc, zinc oxide or mixtures of these substances. In the formulation of powder or spray, it may comprise lactose, talc, silica, aluminum hydroxide, calcium silicate, polyamide powder and mixtures of these substances. Spray may additionally comprise the customary propellants, for example, chlorofluorohydrocarbons, propane/butane or dimethyl ether.

The formulation of solution and emulsion may comprise solvent, solubilizer and emulsifier, for example water, ethanol, isopropanol, ethyl carbonate, ethyl acetate, benzyl alcohol, benzyl benzoate, propylene glycol, 1,3-butylglycol, oils, in particular cottonseed oil, groundnut oil, maize germ oil, olive oil, castor oil and sesame seed oil, glycerol fatty esters, polyethylene glycol and fatty acid esters of sorbitan or mixtures of these substances. The formulation of suspension may comprise liquid diluents, for example water, ethanol or propylene glycol, suspending agents, for example ethoxylated isosteary alcohols, polyoxyethylene sorbitol esters and poly oxyethylene sorbitan esters, micocrystalline cellulose, aluminum metahydroxide, bentonite, agar and tragacanth or mixtures of these substances.

The formulation of soap may comprise alkali metal salts of fatty acids, salts of fatty acid hemiesters, fatty acid protein hydrolyzates, isethionates, lanolin, fatty alcohol, vegetable oil, glycerol, sugars or mixtures of these substances.

Furthermore, the cosmetic compositions of this invention may contain auxiliaries as well as carrier. The non-limiting examples of auxiliaries include preservatives, antioxidants, stabilizers, solubilizers, vitamins, colorants, odor improvers or mixtures of these substances The compositions of this invention are significantly effective in whitening and caring (treating and preventing wrinkles) skin originated from the retinol derivative of the formula (I).

The following specific examples are intended to be illustrative of the invention and should not be construed as limiting the scope of the invention as defined by appended claims.

EXAMPLE

Synthesis of Retinol Derivative

In a reactor, bromo acetic acid and 1,3-dicyclohexylcarbodiimide (DCC) were added to retinol (Sigma-Aldrich) dissolved in chloroform and a catalytic amount of 4-dimethylaminopyridine was added, followed by stirring. After completion of reaction, the resultant was filtered, extracted with chloroform and dried over anhydrous magnesium sulfate, followed by filtration and concentration, thus yielding bromo acetic acid retinol ester as oil in yellow color.

L-ascorbic acid (Sigma-Aldrich) were dissolved in of DMSO and of potassium bicarbonate were added, followed by stirring. To the resultant was added bromo acetic acid retinol ester. Upon the completion of the reaction, the mixture was extracted with ethyl acetate and dried over anhydrous magnesium sulfate, followed by filtration and concentration to yield final product as oil in brown color: Anal. Caclc. For $C_{28}H_{38}O_8$ (502.60): C 66.91; H 7.62; O 25.47: found C 67.12; H 7.54; O 25.34

Formulation Example

The cosmetic compositions were made as described in Table I.

TABLE I

| Ingredient | Form. A | Form. B | Form. C | Form. D | Form. E |
|---|---|---|---|---|---|
| Derivative** | 2.0* | — | — | 0.05 | 10.0 |
| Retinol | — | 2.0 | — | — | — |
| L-ascorbic acid | — | — | 2.0 | — | — |
| Propylene glycol | 6.0 | 6.0 | 6.0 | 6.0 | 6.0 |
| Glycerine | 4.0 | 4.0 | 4.0 | 4.0 | 4.0 |
| Triethanol amine | 1.2 | 1.2 | 1.2 | 1.2 | 1.2 |
| Tocopheryl acetate | 3.0 | 3.0 | 3.0 | 3.0 | 3.0 |
| Liquid paraffin | 5.0 | 5.0 | 5.0 | 5.0 | 5.0 |
| Squalane | 3.0 | 3.0 | 3.0 | 3.0 | 3.0 |
| Makadamianut oil | 2.0 | 2.0 | 2.0 | 2.0 | 2.0 |
| Polysorbate 60 | 1.5 | 1.5 | 1.5 | 1.5 | 1.5 |
| Sorbitan sesquinoleate | 1.0 | 1.0 | 1.0 | 1.0 | 1.0 |
| Propyl paraben | 0.1 | 0.1 | 0.1 | 0.1 | 0.1 |
| Carboxyvinyl polymer | 1.0 | 1.0 | 1.0 | 1.0 | 1.0 |
| Pf. Kn-921 | 0.3 | 0.3 | 0.3 | 0.3 | 0.3 |
| Distilled water | Residual amount | Residual amount | Residual amount | Residual amount | Residual amount |
| Total | 100 | 100 | 100 | 100 | 100 |

*expressed as weight percentage
**the retinol derivative of this invention

Experimental Example I

Evaluation of Effect on Collagen Biosynthesis

Human normal fibroblasts (ATCC) were inoculated ($2\times10^4$ cells/well) on 96-well microplate containing DMEM supplemented with FBS and incubated for 24 hours at 37° C. After incubation, the medium in microplate was replaced with fresh DMEM without serum comprising the derivative of this invention, retinol or ascorbic acid and then additional incubation for 48 hours was carried out. Control was not treated with any of the compounds described above. Following incubation, each well was rinsed, fresh DMEM without serum was supplied and then additional incubation for 24 hours was performed. Then, procollagen type C-peptide obtained from the supernatant of each well was measured using a kit purchased from Takara Co. (Japan) and the measured values were converted to ng/$2\times10^4$ cells, which indicate the amount of collagen newly generated. The results are summarized in Table II.

TABLE II

| | Amount of Collagen Newly Generated (ng/$2 \times 10^4$ cells) | | | |
|---|---|---|---|---|
| Addition Amount | L-ascorbic acid | Retinol | Derivative | Control* |
| 50 μg | 198 | 174 | 215 | 75 |
| 100 μg | 267 | 233 | 290 | 68 |
| 200 μg | 314 | 286 | 349 | 79 |

As indicated in Table II, it was found that the retinol derivative of this invention is much more effective than retinol and ascorbic acid in collagen biosynthesis of human fibroblast. In addition, the retinol derivative of this invention was found to exhibit the effect of enhancing collagen biosynthis in a dose dependent manner.

Experimental Example II

Evaluation of Scavenging Effect on Free Radical

Evaluation of scavenging effect on free radical was performed using DPPH (1,1-diphenyl-2-picryl-hydrazyl, Sigma-Aldrich). 100 µl of each of the substances (the derivative of this invention, retinol and ascorbic acid) diluted to a suitable concentration and 100 µl of 400 µM DPPH solution were consequently added to a 96-well microplate and agitation was performed, followed by reaction for 30 min. at room temperature. Then, absorbance at 520 nm was measured using spectrophotometer. Control contains 100 µl of ethanol in place of the substance to be tested. The scavenging effect on free radical was calculated as following formula: scavenging effect on free radical (%)=100−{(absorbance of sample solution/absorbance of control)×100}

The results are summarized in Table III.

TABLE III

| Substance to be tested | Concentration | Scavenging effect on free radical (%) |
|---|---|---|
| Derivative of this invention | 0.5 mM | 95.7 |
|  | 1 mM | 96.4 |
| Retinol | 0.5 mM | 0.4 |
|  | 1 mM | 1.6 |
| L-ascorbic acid | 0.5 mM | 91.2 |
|  | 1 mM | 91.9 |

As shown in Table III, the present derivative was found to exhibit improved scavenging effect on free radical compared to L-ascorbic acid.

Experimental Example III

Evaluation of Inhibitory Effect on Tyrosinase Activity

A tyrosinase used herein was purchased from Sigma (U.S.A.). Tyrosine as substrate was used as a solution (0.1 mg/ml) dissolved in 0.05 M sodium phosphate buffer (pH 6.8).

0.5 ml of tyrosine solution was placed in a test tube and 0.5 ml of sample solution to be evaluated was added. The test tube was allowed to stand in incubator for 10 min. at 37° C. and then 0.5 ml of tyrosinase (200 U/ml) was added. The reaction was carried out for 10 min at 37° C. As a control group, 0.5 ml of buffer solution was added instead of the sample to be evaluated. The reaction was quenched by placing the test tube on ice and the absorbance of the resultant was measured at 475 nm with spectrophotometer. The inhibitory effect on tyrosinase activity was determined by the equation: inhibition rate on tyrosinase activity (%)=100−{(absorbance of sample/absorbance of control)×100}

The results are shown in Table IV.

TABLE IV

| Sample Conc. (µg/ml) | Inhibition rate on tyrosinase activity (%) | | |
|---|---|---|---|
| | L-ascorbic acid | Retinol | Derivative of this invention |
| 10 | 5.1% | 0.6% | 8.1% |
| 20 | 9.8% | 1.1% | 10.7% |
| 50 | 13.2% | 3.2% | 13.8% |
| 100 | 22.5% | 3.9% | 32.9% |
| 200 | 34.8% | 5.6% | 47.1% |
| 500 | 62.4% | 9.2% | 78.8% |

As indicated in Table IV, the derivative of this invention was found to show higher inhibition rate on tyrosinase activity than ascorbic acid. Therefore, it will be appreciated that the inhibitory effect on melanin formation of the present derivative is higher than that of ascorbic acid.

Experimental Example IV

Evaluation of Whitening Effect

Whitening effect of the present derivative was evaluated through practical use test. Test group aged 19-40 consisted of thirty women who showed relatively dark skin. Measurement of whitening effect was performed at an interval of 2 weeks using Minolta CR 300 for 8 weeks. Each of the formulations described in Table I (Formulations A-E) was applied to each of 5 portions (1×1 cm) of forearm. The results are represented in FIG. 1.

As shown in FIG. 1, the formulations comprising the present derivative (Form. A, D and E) represent much higher □L value than control group and the formulations A and E are revealed to show higher □L value than L-ascorbic acid. Therefore, it is known that the present derivative has improved whitening effect compared to L-ascorbic acid.

Experimental Example V

Evaluation of Skin Irritation

In order to confirm whether the formulations described in Table I (Form. A-E) induce a skin irritation, the test was carried out. Test group consisted of fifty healthy adults. Each of the formulations (about 0.1 g) as patch form was applied to a portion (5×20 cm) in forearm of testee for 24 hours and then removed. After 1 hour and 24 hours, a skin condition was evaluated with naked eye, of which results are indicated in Table V. In Table V, the skin condition was evaluated as the following criteria: "−": not observing particular symptoms such as erythema; "+−": becoming slightly reddish; "+": becoming significantly reddish; and "++": becoming severely reddish and swollen.

In Table V, the irritation rates was calculated as the following equation: irritation rate={[No. of (+−)×1+No. of (+)×2+No. of (++)×3]/[No. of testee×3]}×100

TABLE V

| Formulation | No. of testee | Evaluation Result | | | | Irritation Rate (%) |
|---|---|---|---|---|---|---|
| | | ++ | + | +− | − | |
| A | 50 | − | − | 2 | 48 | 1.3 |
| B | 50 | − | − | 3 | 47 | 2.0 |

TABLE V-continued

| Formulation | No. of testee | Evaluation Result ++ | + | +− | − | Irritation Rate (%) |
|---|---|---|---|---|---|---|
| C | 50 | − | − | 2 | 48 | 1.3 |
| D | 50 | − | − | 1 | 49 | 0.7 |
| E | 50 | − | 1 | 4 | 45 | 4.0 |

As known in Table V, the formulation A comprising the present derivative shows relatively low irritation rate compared to other formulations. It is notable that the formulation A exhibits much lower irritation rate than the formulation B comprising retinol.

Experimental Example VI

Evaluation of Wrinkle Treatment

Forty-five women aged above 30 (mean age 33.7) were classified to 3 groups. To group A, was applied the formulation A, to group B the formulation B and to group C the formulation D. Applied portion was eye rims with wrinkles and the time period for application was 12 weeks. After application, the objective evaluation was made by well-trained tester and the subjective evaluation was made by testee oneself. The evaluation of wrinkle treatment was made according to 7 levels ranging from −3 (showing very severe deterioration of wrinkle) to 3 (showing remarkable amelioration of wrinkle). The results are summarized in Tables VI and VII.

TABLE VI

Objective Evaluation of Wrinkle Treatment

| | Level of Wrinkle Treatment | | | | | |
|---|---|---|---|---|---|---|
| | A | | B | | D | |
| Testee | 0 day* | 12 wk** | 0 day | 12 wk | 0 day | 12 wk |
| Testee 1 | 0 | 3 | 0 | 3 | 0 | 2 |
| Testee 2 | 0 | 2 | 0 | 3 | 0 | 3 |
| Testee 3 | 0 | 3 | 0 | 2 | 0 | 2 |
| Testee 4 | 0 | 3 | 0 | 3 | 0 | 2 |
| Testee 5 | 0 | 3 | 0 | 3 | 0 | 3 |
| Testee 6 | 0 | 3 | 0 | 3 | 0 | 3 |
| Testee 7 | 0 | 3 | 0 | 2 | 0 | 3 |
| Testee 8 | 0 | 2 | 0 | 2 | 0 | 2 |
| Testee 9 | 0 | 2 | 0 | 3 | 0 | 2 |
| Testee 10 | 0 | 3 | 0 | 3 | 0 | 3 |
| Testee 11 | 0 | 3 | 0 | 2 | 0 | 2 |
| Testee 12 | 0 | 3 | 0 | 3 | 0 | 2 |
| Testee 13 | 0 | 3 | 0 | 3 | 0 | 2 |
| Testee 14 | 0 | 3 | 0 | 3 | 0 | 3 |
| Testee 15 | 0 | 2 | 0 | 2 | 0 | 3 |
| Mean | 0 | 2.73 | 0 | 2.67 | 0 | 2.47 |

*level of wrinkle treatment at the beginning time of the test
**level of wrinkle treatment after 12 weeks from the test

TABLE VII

Subjective Evaluation of Wrinkle Treatment

| | Level of Wrinkle Treatment | | | | | |
|---|---|---|---|---|---|---|
| | A | | B | | D | |
| Testee | 0 day* | 12 wk** | 0 day | 12 wk | 0 day | 12 wk |
| Testee 1 | 0 | 3 | 0 | 2 | 0 | 3 |
| Testee 2 | 0 | 2 | 0 | 3 | 0 | 2 |
| Testee 3 | 0 | 3 | 0 | 3 | 0 | 2 |
| Testee 4 | 0 | 3 | 0 | 3 | 0 | 3 |
| Testee 5 | 0 | 3 | 0 | 3 | 0 | 3 |
| Testee 6 | 0 | 3 | 0 | 2 | 0 | 3 |
| Testee 7 | 0 | 3 | 0 | 3 | 0 | 2 |
| Testee 8 | 0 | 2 | 0 | 2 | 0 | 3 |
| Testee 9 | 0 | 2 | 0 | 3 | 0 | 3 |
| Testee 10 | 0 | 3 | 0 | 3 | 0 | 2 |
| Testee 11 | 0 | 3 | 0 | 2 | 0 | 2 |
| Testee 12 | 0 | 3 | 0 | 2 | 0 | 3 |
| Testee 13 | 0 | 3 | 0 | 3 | 0 | 2 |
| Testee 14 | 0 | 3 | 0 | 3 | 0 | 3 |
| Testee 15 | 0 | 2 | 0 | 3 | 0 | 2 |
| Mean | 0 | 2.73 | 0 | 2.67 | 0 | 2.53 |

*level of wrinkle treatment at the beginning time of the test
**level of wrinkle treatment after 12 weeks from the test As known in Tables VI and VII, the formulation A containing the present derivative was found to exhibit improved effect on wrinkle treatment, which showed 2.67 and 2.73 in objective and subjective evaluations, respectively.

Experimental Example VII

Evaluation of Formulation Stability

The formulations A, B, C, D and E described in Table I were stored in an opaque container for 12 weeks with keeping constant temperature. Then, the separation and the discoloration levels of the formulations were measured. The separation and the discoloration levels were classified to 6 levels: 0: no change; 1: very slightly discolored (separated); 2: slightly discolored (separated); 3: slightly remarkable discoloration (separated); 4: remarkable discoloration (separated); and 5: very remarkable discoloration (separated)

TABLE VIII

| | Discoloration (Separation) Level | | | | |
|---|---|---|---|---|---|
| Temp. | A | B | C | D | E |
| 45° C. | 0 | 1 | 0 | 0 | 1 |
| 4° C. | 0 | 0 | 0 | 0 | 0 |

As indicated in Table VIII, it was found that the formulation A containing the present derivative is more stable than the formulation B containing retinol. The formulations containing the present derivative was revealed to show a slight discoloration, if the amount of the present derivative is more than 10 wt %.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A retinol derivative represented by the following formula (I):

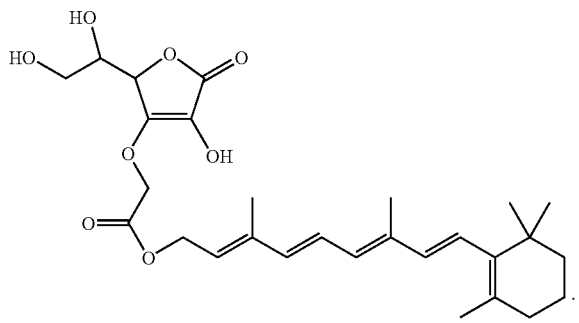

(I)

2. A cosmetic composition comprising:
(a) a cosmetically effective amount of a retinol derivative represented by the following formula (I); and
(b) a cosmetically acceptable carrier:

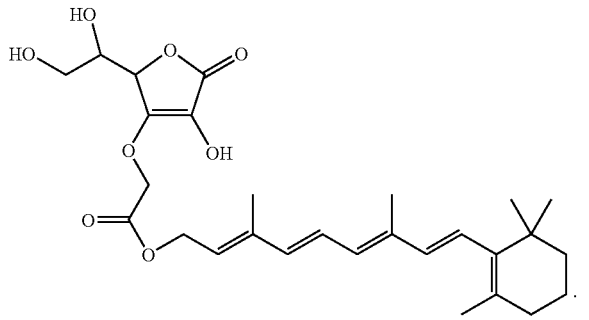

3. The cosmetic composition according to claim 2, wherein the composition has an effect selected from the group consisting of enhancement of collagen biosynthesis, antioxidation, inhibition of tyrosinase activity, skin whitening, treatment of wrinkles and combinations thereof.

4. The cosmetic composition according to claim 2, wherein the retinol derivative is present in an amount of 0.0001-10.0 wt % based on the total weight of the composition.

5. The cosmetic composition according to claim 4, wherein the retinol derivative is present in an amount of 1.0-3.0 wt % based on the total weight of the composition.

6. The cosmetic composition according to claim 2, wherein the cosmetic composition is in the form of one selected from the group consisting of a solution, a suspension, an emulsion, a paste, an ointment, a gel, a cream, a lotion, a powder, a soap, a surfactant-containing cleanser, an oil, a powder foundation, an emulsion foundation, a wax foundation and a spray.

* * * * *